United States Patent [19]
Kele et al.

[11] Patent Number: 4,732,460
[45] Date of Patent: Mar. 22, 1988

[54] BEAM SELECTOR FOR A PHOTOCOAGULATOR

[75] Inventors: Kalman Kele, Scotts Valley; Nubar Manoukian, Cupertino, both of Calif.

[73] Assignee: Coherent, Inc., Palo Alto, Calif.

[21] Appl. No.: 881,135

[22] Filed: Jul. 1, 1986

[51] Int. Cl.$^4$ .................. G02B 27/00; G02B 7/18; B23K 26/00

[52] U.S. Cl. .................. 350/486; 350/618; 350/622; 350/623; 350/633; 350/287; 219/121 LG; 219/121 LS; 219/121 LU; 219/121 LV; 128/303.1; 372/70

[58] Field of Search .............. 350/486, 618, 622, 623, 350/624, 633, 632, 286; 128/303.1; 219/121 LV, 121 LU, 121 LS, 121 LG, 121 LN, 121 LM, 121 L

[56] References Cited

U.S. PATENT DOCUMENTS 3,924,937 12/1975 Munroe et al. ............... 350/486
4,550,240 10/1985 Toida et al. ............... 219/121 LV

FOREIGN PATENT DOCUMENTS 144889 11/1981 Japan ............... 219/121 LV

*Primary Examiner*—Jon W. Henry
*Attorney, Agent, or Firm*—Limbach, Limbach & Sutton

[57] ABSTRACT

The subject invention relates to an apparatus for selectively intercepting and redirecting a beam from a laser. The apparatus is particularly suited for use in a photocoagulator having an argon laser and a dye laser which are rigidly mounted to a housing. A set of fixed optical elements are provided for directing the beam of the argon laser to the cavity of the dye laser to pump the dye laser. The subject apparatus selectively intercepts and redirects the argon laser beam from its initial path to the dye laser to an alternative path out of the photocoagulator. In this manner, the wavelengths available from the argon laser can also be utilized to perform surgery. The apparatus for selecting the argon beam includes a pivotally mounted frame which is easily aligned and can reliably maintain that alignment.

36 Claims, 10 Drawing Figures

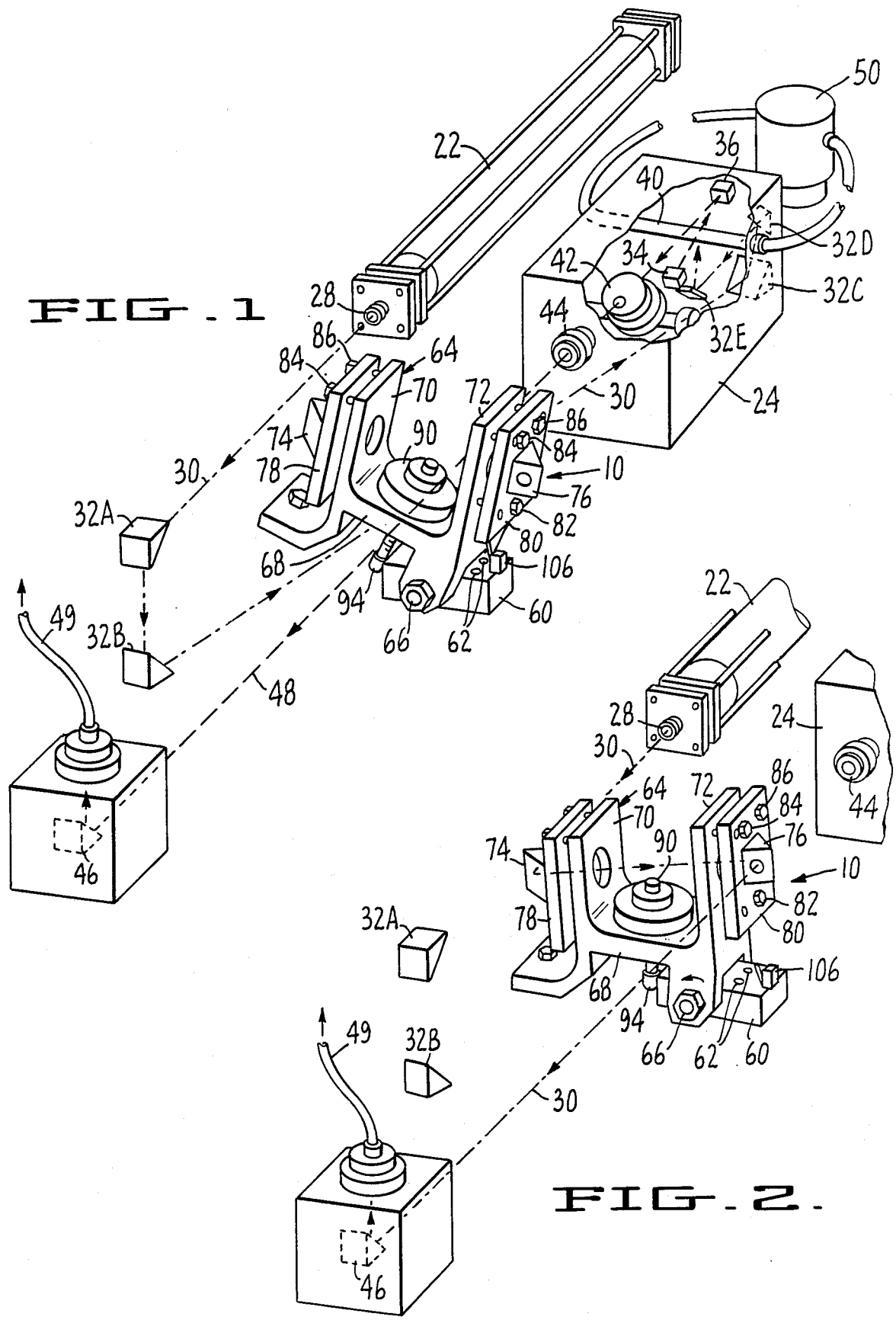

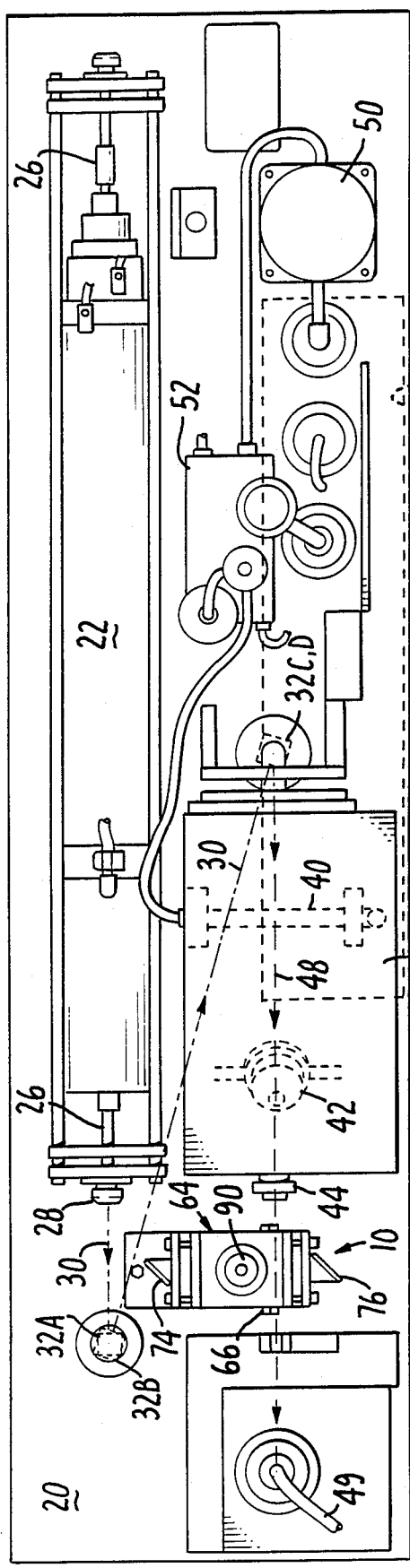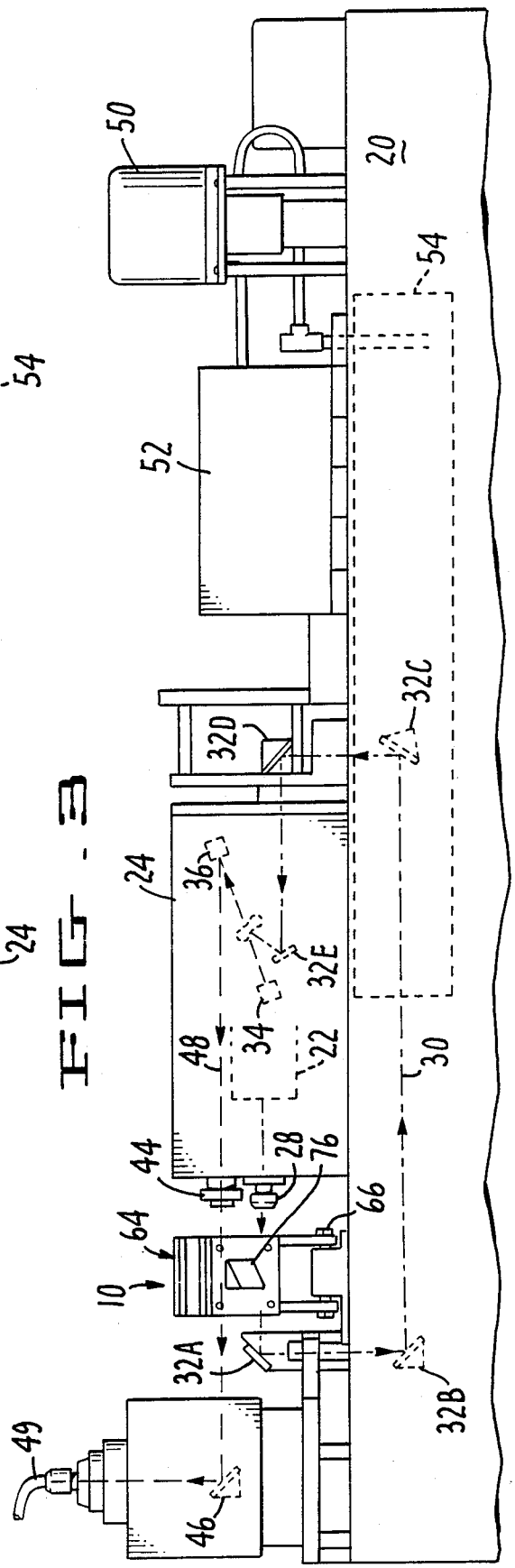
FIG. 3
FIG. 4

BEAM SELECTOR FOR A PHOTOCOAGULATOR

TECHNICAL FIELD

The subject invention relates to an apparatus for selectively intercepting and redirecting a laser beam. The subject apparatus is particularly suited for use in a photocoagulator.

BACKGROUND OF THE INVENTION

The subject invention relates to a beam selector for a laser and in particular, to an improvement in a medical laser photocoagulator. For quite some time, surgeons have been using the beam from a laser source to perform delicate eye surgery. One of the advantages of using a laser beam for surgery is that it can be tightly focused on the area to be treated. Another advantage is that different tissues in the eye absorb different wavelengths of light. Therefore, a beam which will pass harmlessly through the cornea can be used to treat retinal tissue at the back of the eye. In use, the doctor will select a particular wavelength radiation which will be highly absorbing in the tissue to be treated, while not causing damage to surrounding tissues.

For quite some time, gaseous ion lasers were used in medical photocoagulators. In a gaseous ion laser, a gas is energized to create an excited state of ions which emit radiation at certain specific wavelengths. Different wavelengths can be generated by using different gases. One of the most common ion lasers used for eye surgery is an argon ion laser. This type of laser produces significant output lines at 488 and 514 nanometers. In contrast, an ion laser filled with krypton gas will generate significant power at laser lines having wavelengths 531, 568, 647 and 676 nanometers. In some photocoagulators, both an argon and a krypton gas laser are used to provide a wider range of wavelength lines.

About one and a half years ago, the assignee of the subject invention, Coherent, Inc., introduced a new photocoagulator which combined an ion laser and a dye laser. In a dye laser, the laser cavity includes a fast flowing stream of fluid which is colored with an organic dye. The laser cavity is excited or pumped using another laser, such as an ion laser or an eximer laser. One of the primary advantages of a dye laser is that the output can be tuned. Thus, rather than merely producing individual lines similar to an ion laser, a dye laser is capable of generating laser radiation over a range of wavelengths. The present dye laser used in the assignees photocoagulator emits radiation across a spectrum from 577 to 630 nanometers.

In the combination ion and dye laser system, marketed as the 900 series photocoagulator by Coherent, Inc., the argon ion laser or primary laser performs two alternate functions. In one mode, the beam from the argon laser is used to pump the cavity of the dye laser. In the other mode, the argon laser beam itself is used for surgery. In this manner, the shorter wavelength argon lines are available to the surgeon.

In order to achieve this result, the optics in the photocoagulator are required to direct the argon ion laser beam along one of two paths. In one path, the argon beam is channeled directly out of the device through a fiber optic wand. The optics are also capable of directing the argon ion laser beam along a second path to pump the dye laser.

The optical alignment necessary to deliver the argon laser beam to the dye laser is critical. Accordingly, the fixed optics in the device are typically set to direct the argon ion laser beam directly to the cavity of the dye laser. The optics further include a movable member for selectively intercepting and redirecting the argon beam to the fiber optic input of the photocoagulator. Even though alignment of the beam along this second path is less critical than the alignment required to pump the dye laser, it nonetheless must be accurately controlled in order to properly deliver the laser beam to the output portion of the device.

In the prior art device described above, a mirrored reflector was mounted on a translatable car which was movable into the path of the argon ion laser beam. The car was journalled on races that included precision made ball bearings. The translatable car was difficult to fabricate and expensive. In addition, the device was relatively heavy, requiring a strong motor to actuate. It was also found to be difficult to ensure that the tracks maintained perfect alignment as the reflector was moved into and out of the path of the argon ion laser beam. Thus, it could be desirable to provide an improved beam selector which overcomes the problems found in the translatable car of the prior art.

As mentioned above, some photocoagulators have both an argon ion laser and a krypton ion laser. In these devices, only one of the two lasers is used at any particular time. A beam selection system must still be provided to insure that both laser beams will ultimately travel along the same path to the output of the device. In the prior art argon/krypton photocoagulators, this result was achieved through the use of a fixed position beam splitter or dichroic mirror which selectively passes different laser wavelength lines. The design and fabrication of such optical elements can be expensive. Furthermore, it is difficult to design a single splitter which will reflect all of the argon laser lines but transmit all of the krypton laser lines. Nonetheless, the latter approach was still preferred over the complex translatable car used in the argon/dye photocoagulator described above. However, if an improved movable selector were designed, it could be used to replace the complex and expensive optical beam splitters.

Accordingly, it is an object of the subject invention to provide a new and improved apparatus for selectively intercepting and redirecting a laser beam.

It is another object of the subject invention to provide a new and improved apparatus for accurately intercepting and redirecting a laser beam in a photocoagulator.

It is a further object of the subject invention to provide a new and improved apparatus for selectively redirecting a laser beam that is lightweight in construction and can be easily moved.

It is still another object of the subject invention to provide a new and improved apparatus for intercepting and redirecting a laser beam which is simple to manufacture yet is highly accurate.

SUMMARY OF THE INVENTION

The apparatus subject invention is designed to intercept and redirect a laser beam. As such, the apparatus may find use in a number of commercial situations. For example, the expense of a complete laser system may restrict a surgeon's ability to purchase more than one such system. Yet, a typical doctor's office may have many treatment rooms. By utilizing the apparatus of the subject invention, it would be possible to house the laser system in one room and redirect its single beam to different treatment rooms.

While the apparatus of the subject may function in a wide variety of environments as indicated above, it is particularly suitable for use in medical photocoagulators having a pair of lasers. The apparatus includes a frame means which is mounted to a support means. The frame means is generally U-shaped in configuration with a base and two upstanding legs. A pair of mounting plates are adjustably attached to the upstanding legs of the frame means. A pair of mirrors are, in turn, connected to the adjustably attached mounting plates. Each of the mirrors is independently adjustable via the mounting plates to allow alignment of the primary laser beam.

In accordance with the subject invention, the frame means is movable between first and second positions. In the first, inactive position, the frame will be located out of the path of both the first and second laser beams. Where an argon and krypton laser combination is used, the beam from the argon laser will be shut off and the krypton beam is sent to the output of the device. In the case of a pump and dye laser combination, the fixed optics of the system will direct the pump laser to the cavity of the dye laser to provide the pump source. The fixed optics will also direct the dye laser beam to the output of the device.

When the frame is pivoted into the second, active position, the first laser beam is intercepted and redirected to the output of the device. The movement of the apparatus is limited to pivoting around a single axis. By this arrangement, the alignment of the beam from the first laser is far easier to initialize and maintain even after numerous cycles of movement of the selector.

Further objects and advantages of the subject invention will become apparent from the following detailed description taken in conjunction with the drawings, in which:

BRIEF DESCRIPTION OF THE DRAWINGS

FIG. 1 is a perspective view of the primary components of a photocoagulator, including an argon laser, a dye laser and optical elements, and illustrating the beam selector of the subject invention oriented to allow the argon laser beam to pump the dye laser.

FIG. 2 is a perspective view, similar to FIG. 1, where the beam selector of the subject invention is in the second position for intercepting and redirecting the argon laser beam to the output of the device.

FIG. 3 is a top plan view of the photocoagulator wherein the beam selector of the subject invention is in the inactive position.

FIG. 4 is a side elevational view of the photocoagulator wherein the beam selector of the subject invention is in the inactive position.

DETAILED DESCRIPTION OF THE PREFERRED EMBODIMENT

Figure 5:
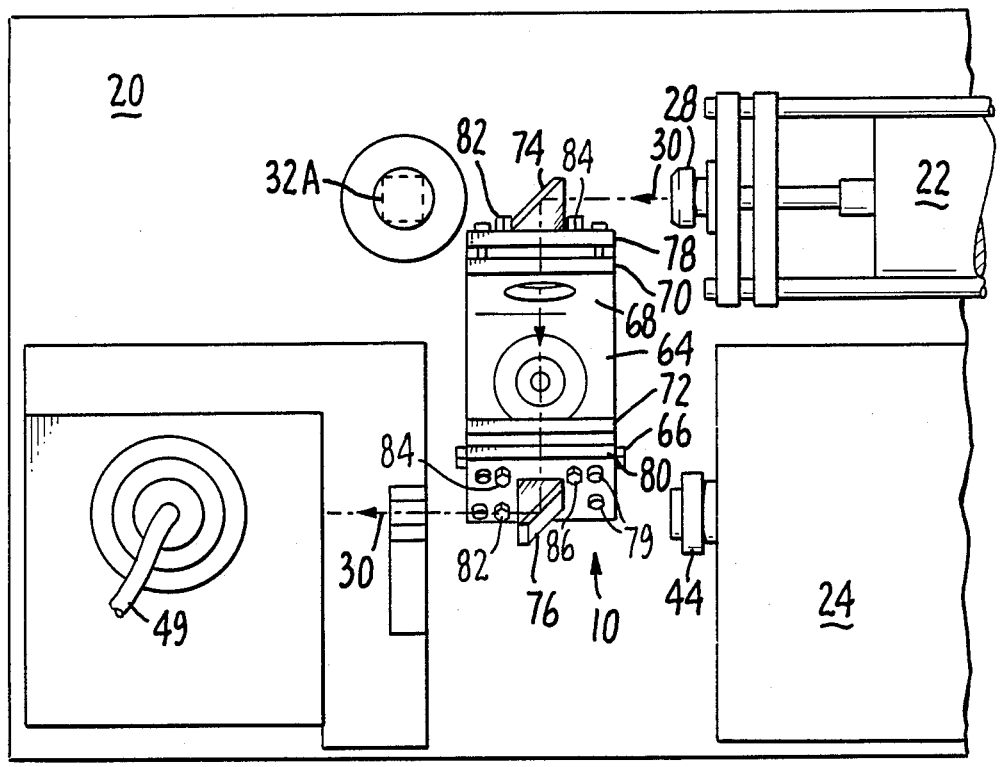
FIG. 5 is a top plan view of the photocoagulator illustrating the beam selector in a position for intercepting the argon ion laser beam.
Figure 6:
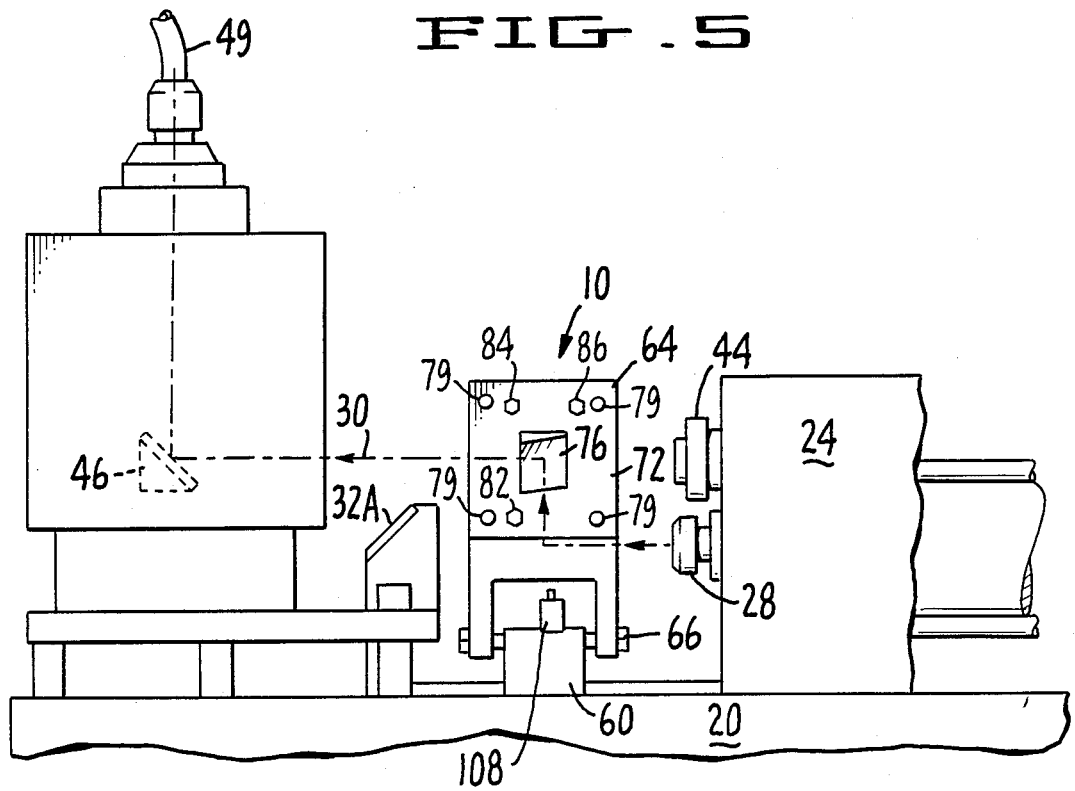
FIG. 6 is a side view of the photocoagulator also illustrating the beam being intercepted and redirected by the beam selector of the subject invention.

Illustrated in FIGS. 1 through 4, are the main components of a photocoagulator, in which the subject beam selector 10 may be utilized. More specifically, the photocoagulator includes a housing 20 to which is rigidly mounted an argon laser 22 and a dye laser 24. The argon laser may be of the type shown in U.S. Pat. No. 4,378,600, issued Mar. 29, 1983 to Hobart and marketed by Coherent, Inc. under the trademark "INNOVA".

An argon ion laser 22 is preferred since the output lines therefrom are particularly suitable for photocoagulation. It would be possible to substitute another type of primary laser as long as it was suitable for pumping the dye laser. The argon laser 22 includes a pair of windows 26, mounted at Brewster's angle and an output coupler 28 through which the beam 30 is transmitted. The argon laser produces blue and green lines at 488 and 514 nanometers, respectively.

In the preferred embodiment, the photocoagulator includes a plurality of fixed mirrors 32A, 32B, 32C, 32D, and 32E for directing the argon ion laser beam 30 to the cavity of the dye laser 24. The cavity of the dye laser is defined by high reflective mirror 34, fold mirror 36 and output coupler 44. A stream of liquid 40, which includes an organic dye, is pumped through the dye laser cavity in a non-collinear pump design as described in U.S. Pat. No. 3,873,941, asssigned to the same assignee as the subject invention. The energy from the argon laser functions to pump energy into the dye, causing it to lase. A birefringent filter tuning plate 42 is provided for adjusting the output wavelength of the laser light. A description of a birefringent filter can be found in U.S. Pat. No. 3,868,592, assigned to the same assiqnee as the subject invention. The beam 48 from the dye laser is passed through output coupler 44 and to the output mirror 46 of the photocoagulator. Output mirror 46 directs the light beam to the input of the fiber optic cable 49.

The illustrated dye laser 24 is of a conventional type including a pump 50 for circulating the dye, a heat exchanger and filter system 52, and a reservoir 54. In the preferred embodiment, the dye utilized is Rhodamine 6G, which when pumped by a blue/green laser beam, produces a variable output in the 577 to 630 nanometer range.

Where the photocoagulator consists only of an argon and a krypton laser, they can be located in a side by side relationship similar to the argon and dye lasers as shown above. In this case, none of the fixed optics for directing the argon beam to the dye laser would be necessary. The argon and krypton lasers are operated independently and the beam selector functions to permit both laser beams to travel the same path as they leave the device. Since the beam selector apparatus is identical in both types of photocoagulators, it will only be described with reference to the argon/dye combination.

In accordance with the subject invention, a new and improved apparatus 10 is provided for selectively intercepting and redirecting the argon laser beam 30 to the output mirror 46 of the photocoagulator. The apparatus 10, which is shown in greater detail in FIGS. 7 through 10, includes a support 60 which is rigidly mounted with respect to the argon and dye lasers. The rigid connection is provided by a plurality of screws 62 which also can provide some coarse adjustment of the selector 10.

Selector 10 further includes a frame 64 which is pivotally mounted to the support 60. The pivotal mounting is defined by a precision shaft 66, which is passed through bearings in the frame. Frame 64 is generally U-shaped in configuration having a planar base 68 and two upstanding legs 70 and 72.

The means for intercepting and redirecting the argon laser beam 30 is defined by a pair of mirrors 74 and 76. The connection of the mirrors to the frame is defined by a pair of adjustable mounting plates 78 and 80. Each mounting plate is connected to the associated leg of the frame by a plurality of screws 79. The ends of screws 79 are engaged with threaded holes in legs 70, 72. The heads of screws 79 are spring loaded and received in oversize bores formed in plates 78, 80. In this manner, the plates can float with respect to the legs. A pair of sheet metal strips 81 (shown only in FIG. 7 for clarity) are provided to prevent the relative rotation between plates 78, 80 and legs 70, 72.

The subject assembly further includes three adjustment screws 82, 84 and 86 which are threaded through plates 78 and 80 and abut legs 70 and 72. The three screws are arranged in a right triangle configuration. By rotating the screws, the angular position of the plates can be varied. More specifically, if screw 86 is rotated, the plate will pivot about a line defined between screws 82 and 84. If screw 82 is rotated, the plate will pivot about a line defined between screws 84 and 86. The adjustment of the plates will vary the angle of the mirror faces, and therefore the alignment of the beam 30. As seen best in FIG. 9, both legs 70 and 72, as well as the mounting plates 78 and 80, includes openings through which the beam 30 of the argon laser may pass.

It would be possible to provide frame 64 with only a single mirror to intercept and redirect the argon ion laser beam. In this case, a second, adjustable mirror would have to be mounted on the housing, since at least two adjustable mirrors are necessary to insure that the argon beam 30 is coaxial with the dye laser beam 48. However, it is believed that the illustrated embodiment, with two adjustable mirrors both mounted on the frame, provides superior performance and ease of adjustment.

Figure 7:
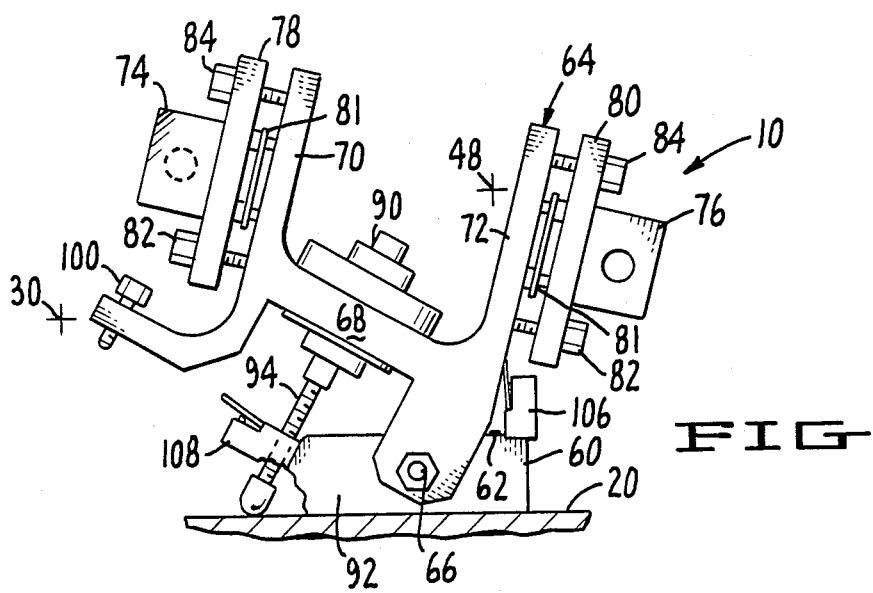
FIG. 7 is a side elevational view of the beam selector of the subject invention illustrated in the first, inactive position.
Figure 9:
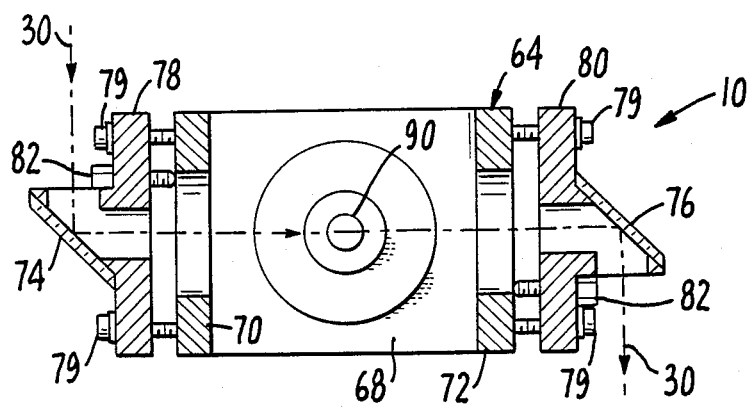
FIG. 9 is a cross sectional view, taken along the lines 9—9 in FIG. 8, of the beam selector of the subject invention.
Figure 8:
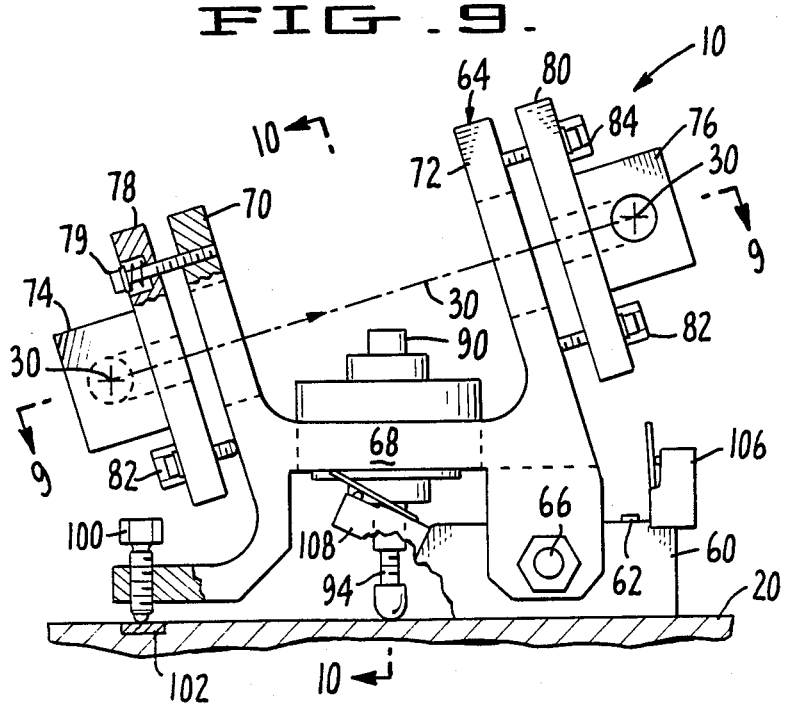
FIG. 8 is a side elevational view of the beam selector of the subject invention oriented in the second, active position.
Figure 10:
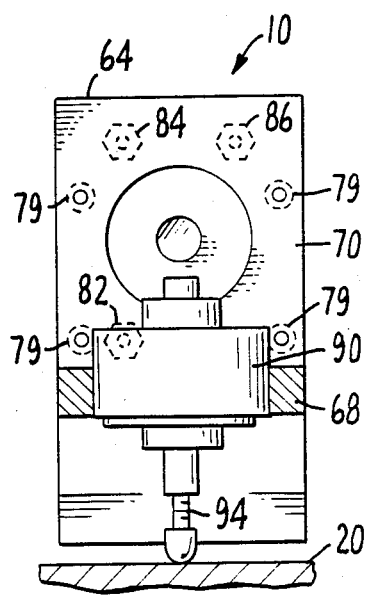
FIG. 10 is a cross sectional view, taken along the lines 10—10 in FIG. 8, of the beam selector of the subject invention.

The apparatus 10 further includes a means for moving the frame 64 between the first and second positions. The means for moving the apparatus may be relatively simple due to the light weight of the apparatus and its low friction, pivotal mounting. As illustrated in FIGS. 7 and 8, the means includes a linear actuator 90. In operation, when the frame is to be raised to the position shown in FIG. 7, linear actuator 90 will be activated, causing a plunger 94 to extend in a manner to pivot the frame about shaft 66. In this position, (also shown in FIGS. 1, 3 and 4), mirror 74 is inactive and the entire selector 10 is located out of the paths of both beams 30 and 48. When the selector is clear of the argon beam 30, the fixed optics of the photocoagulator (mirrors 32) will direct the argon beam 30 to the cavity of the dye laser.

When the argon beam 30 is to be used directly for photocoagulation, the plunger 94 of linear actuator 90 is retracted, causing the frame to move back into a downward position as illustrated in FIGS. 2, 5, 6 and 8. In this orientation, beam 30 will strike the reflecting surface of mirror 74 and be deflected to mirror 76. Mirror 76 will then redirect beam 30 to the output mirror 46 of the photocoagulator. As noted above, adjustment of the position of the beam can be made by rotating screws 84 and 86 on mounting plates 78 and 80.

A further mechanism for adjusting the coarse position of frame 64 is provided by a screw 100, having a hardened tip, which is threaded through a portion of frame 64, as best seen in FIG. 8. By rotating screw 100, the resting position of frame 64 can be regulated. In the preferred embodiment, a hardened carbide pad 102 is affixed to the surface of housing 20, in alignment with the hardened tip of screw 100. In this manner, repeated movement of the frame to the downward, active position will not wear out the upper surface of the housing causing the selector to become misaligned.

As seen best in FIGS. 7 and 8, it is also desirable to provide a pair of microswitches 106 and 108 for sensing the position of the frame 64. As illustrated in FIG. 7, when frame 64 is in the upper, inactive position, microswitch 106 will be activated such that the electronic control circuit (not shown) of the system will recognize that the argon beam 30 is available to pump the dye laser. Conversely, when the frame is in the downward position as shown in FIG. 8, microswitch 108 will be activated indicating that the argon beam is directly available for photocoagulation. During the movement of the frame 64 between the first and second positions, neither switch is activated which will indicate that the frame has not yet been properly positioned.

In operation, the optics of the system are initially adjusted to align the beam 30 of the argon laser into the cavity of the dye laser. Then the beam 48 of the dye laser is adjusted so it is properly aligned with the output mirror 46. Thereafter, the beam selector 10 is moved into the downward, active position. Coarse adjustment screw 100 is rotated until beam 30 is roughly centered on mirror 74. Screws 82 and 86 are then rotated, one plate at a time, to make sure that argon beam 30 is coaxial with the dye beam 48. The subject beam selector 10 therefore provides a low cost, lightweight, simple expedient for selectively intercepting and redirecting a laser beam which can reliably hold its alignment.

While the subject invention has been described with reference to a preferred embodiment, various other changes and modifications could be made therein, by one skilled in the art, without varying from the scope and spirit of the subject invention as defined by the appended claims.

We claim:

1. An apparatus for selectively intercepting and redirecting the beam from a laser comprising:
   support means;
   frame means pivotally mounted to said support means and movable between a first and a second position;
   means for moving said frame means between said first and second positions; and
   a pair of spaced apart mirrors mounted to said frame means, said mirrors being independently adjustable to facilitate the aiming of the beam from the laser, said mirrors being mounted at a location such that when said frame means is in said first position, said mirros are positioned out of the path of the beam from said laser and when said frame means is in said second position, said mirrors intercept and redirect the beam from said laser along a different path.

2. An apparatus as recited in claim 1 wherein said frame means has a generally U-shaped configuration with a base and two upstanding legs.

3. An apparatus as recited in claim 2 wherein each of said legs includes a mounting plate to which is attached one of said two mirrors.

4. An apparatus as recited in claim 3 wherein each said mounting plate is adjustably connected to the associated leg.

5. An apparatus as recited in claim 4 wherein said mounting plate includes three adjustment screws for connecting said mounting plate to the associated leg.

6. An apparatus as recited in claim 2 wherein said pivotal connection between said support means and said frame means is located on the base of said frame means near one of said legs.

7. An apparatus as recited in claim 1 further including a means adjusting the coarse position of said frame means.

8. An apparatus as recited in claim 7 wherein said support means is mounted to a housing and wherein said means for adjusting the coarse position of said frame means is defined by an adjustment screw, threaded through said frame means and located in a manner to abut said housing when said frame means is located in the downward resting position.

9. An apparatus as recited in claim 1 further including a means for sensing the position of the frame means.

10. An apparatus as recited in claim 9 wherein said means for sensing the position of said frame means is defined by microswitches.

11. In a laser system including a first laser and a second laser rigidly mounted to a housing, and wherein said system includes optical means for alternately directing the beam from one of the two lasers to the output of the systems, said optical means including an apparatus for selectively intercepting and redirecting the beam from the first laser, said apparatus comprising:
    frame means pivotally mounted with respect to said housing and movable between a first and a second position;
    means for moving said frame means between said first and second positions; and
    a pair of spaced apart mirrors mounted to said frame means, said mirrors being independently adjustable to facilitate the aiming of the beam from the first laser, said mirros being mounted at a location such that when said frame means is in said first position, said mirrors are positioned out of the path of the beam of both said first and second lasers permitting the beam from the second laser to travel along a path leading to the output of the system and when said frame means is in said second position, said mirrors intercept and redirect the beam from said first laser along a path leading to the output of the system.

12. An apparatus as recited in claim 11 wherein said frame means has a generally U-shaped configuration with a base and two upstanding legs.

13. An apparatus as recited in claim 12 wherein each of said legs includes a mounting plate to which is attached one of said two mirrors.

14. An apparatus as recited in claim 13 wherein each said mounting plate is adjustably connected to the associated leg.

15. An apparatus as recited in claim 14 wherein said mounting plate includes three adjustment screws for connecting said mounting plate to the associated leg.

16. An apparatus as recited in claim 12 further including a support means which is rigidly connected to said housing and wherein said frame means is pivotally connected to said support means.

17. An apparatus as recited in claim 16 wherein said pivotal connection between said support means and said frame means is located on the base of said frame means near one of said legs.

18. An apparatus as recited in claim 11 further including a means adjusting the coarse position of said frame means.

19. An apparatus as recited in claim 18 wherein said means for adjusting the coarse position of said frame means is defined by an adjustment screw, threaded through said frame means and located in a manner to abut said housing when said frame means is located in the downward resting position.

20. An apparatus as recited in claim 11 further including a means for sensing the position of the frame means.

21. An apparatus as recited in claim 20 wherein said means for sensing the position of said frame means is defined by microswitches.

22. An apparatus as recited in claim 11 wherein said second laser is a dye laser and wherein when said frame means is in said first position, the path of said first laser terminates in the cavity of the dye laser to provide a pump source.

23. In a laser system including a primary laser and a dye laser where the beam from the primary laser is used either alone or to pump the dye laser, and wherein said primary and dye lasers are rigidly mounted to a housing, and wherein said system includes optical means for directing the beam from the primary laser along one of two paths, with one path terminating in the cavity of said dye laser to provide a pump source, said optical means including an apparatus for selectively intercepting and redirecting the beam from the primary laser along one of said two paths, said apparatus comprising:
    frame means pivotally mounted with respect to said housing and movable between a first and a second position;
    means for moving said frame means between said first and second positions; and
    reflector means, mounted to said frame means at a location such that when said frame means is in said first position, said reflector means is positioned to permit the beam from the primary laser to travel along the first path and when said frame means is in said second position, said reflector means intercepts and redirects the beam from said primary laser along said second path.

24. An apparatus as recited in claim 23 wherein said reflector means is defined by a pair of spaced apart mirrors, each of said mirrors being independently adjustable to facilitate the aiming of the primary laser beam.

25. An apparatus as recited in claim 24 wherein said frame means has a generally U-shaped configuration with a base and two upstanding legs.

26. An apparatus as recited in claim 25 wherein each of said legs includes a mounting plate to which is attached one of said two mirrors.

27. An apparatus as recited in claim 26 wherein each said mounting plate is adjustably connected to the associated leg.

28. An apparatus as recited in claim 27 wherein said mounting plate includes three adjustment screws for connecting said mounting plate to the associated leg.

29. An apparatus as recited in claim 25 further including a support means which is rigidly connected to said housing and wherein said frame means is pivotally connected to said support means.

30. An apparatus as recited in claim 29 wherein said pivotal connection between said support means and said frame means is located on the base of said frame means near one of said legs.

31. An apparatus as recited in claim 23 further including a means adjusting the coarse position of said frame means.

32. An apparatus as recited in claim 31 wherein said means for adjusting the coarse position of said frame means is defined by an adjustment screw, threaded through said frame means and located in a manner to abut said housing when said frame means is located in the downward resting position.

33. An apparatus as recited in claim 23 further including a means for sensing the position of the frame means.

34. An apparatus as recited in claim 33 wherein said means for sensing the position of said frame means is defined by microswitches.

35. An apparatus for selectively intercepting and redirecting the beam from a laser comprising:
- a support means mounted to a housing;
- frame means pivotally mounted to said support means and movable between a first and a second position;
- means for moving said frame means between said first and second positions one of said positions defining a downward resting position;
- reflector means, mounted to said frame means at a location such that when said frame means is in said first position, said reflector means is positioned out of the path of the beam from said laser and when said frame means is in said second position, said reflector means intercepts and redirects the beam from said laser along a different path; and
- means for adjusting the coarse position of said frame means, said means being defined by an adjustment screw, threaded through said frame means and located in a manner to abut said housing when said frame means is located in the downward resting position.

36. In a laser system including a first laser and a second laser rigidly mounted to a housing, and wherein said system includes optical means for alternately directing the beam from one of the two lasers to the output of the system, said optical means including an apparatus for selectively intercepting and redirecting the beam from the first laser, said apparatus comprising:
- frame means pivotally mounted with respect to said housing and movable between between a first and a second position;
- means for moving said frame means between said first and second positions one of said positions defining a downward resting position;
- reflector means, mounted to said frame means at a location such that when said frame means is in said first position, said reflector means is positioned out of the path of the beams of both said first and second lasers permitting the beam from the second laser to travel along a path leading to the output of the system and when said frame means is in said second position, said reflector means intercepts and redirects the beam from said first laser along a path leading to the output of the system; and
- means for adjusting the coarse position of said frame means, said means being defined by an adjustment screw, threaded through said frame means and located in a manner to abut said housing when said frame means is located in the downward resting position.

* * * * *